(12) United States Patent
Ionasec et al.

(10) Patent No.: US 9,179,890 B2
(45) Date of Patent: Nov. 10, 2015

(54) MODEL-BASED POSITIONING FOR INTRACARDIAC ECHOCARDIOGRAPHY VOLUME STITCHING

(75) Inventors: Razvan Ioan Ionasec, Lawrenceville, NJ (US); Sasa Grbic, Erlangen (DE); Estelle Camus, Mountain View, CA (US); Dorin Comaniciu, Princeton Junction, NJ (US)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 163 days.

(21) Appl. No.: 13/546,066

(22) Filed: Jul. 11, 2012

(65) Prior Publication Data
US 2013/0035596 A1 Feb. 7, 2013

Related U.S. Application Data

(60) Provisional application No. 61/507,703, filed on Jul. 14, 2011.

(51) Int. Cl.
| | |
|---|---|
| *A61B 8/00* | (2006.01) |
| *A61B 8/12* | (2006.01) |
| *A61B 8/08* | (2006.01) |
| *G06T 3/40* | (2006.01) |
| *G06T 7/00* | (2006.01) |

(52) U.S. Cl.
CPC ............ *A61B 8/12* (2013.01); *A61B 8/0883* (2013.01); *A61B 8/483* (2013.01); *G06T 3/4038* (2013.01); *G06T 7/0014* (2013.01); *G06T 7/0032* (2013.01); *G06T 2207/10136* (2013.01); *G06T 2207/20064* (2013.01); *G06T 2207/20076* (2013.01); *G06T 2207/20081* (2013.01); *G06T 2207/30048* (2013.01)

(58) Field of Classification Search
CPC ........ A61B 8/12; A61B 8/0883; A61B 8/483; G06T 3/4038; G06T 7/0014; G06T 7/0032; G06T 2207/10136; G06T 2207/20064; G06T 2207/20076; G06T 2207/20081; G06T 2207/30048
USPC ........................... 600/437–469; 382/128–132
See application file for complete search history.

(56) References Cited

U.S. PATENT DOCUMENTS

| | | | | |
|---|---|---|---|---|
| 5,396,890 | A * | 3/1995 | Weng | 600/443 |
| 6,895,267 | B2 * | 5/2005 | Panescu et al. | 600/424 |
| 6,950,689 | B1 * | 9/2005 | Willis et al. | 600/407 |
| 7,693,563 | B2 * | 4/2010 | Suresh et al. | 600/407 |
| 7,806,829 | B2 * | 10/2010 | Hauck | 600/466 |
| 7,940,972 | B2 * | 5/2011 | Wildes et al. | 382/128 |
| 8,057,394 | B2 * | 11/2011 | Dala-Krishna | 600/466 |
| 8,224,432 | B2 * | 7/2012 | MacAdam et al. | 600/523 |
| 8,303,505 | B2 * | 11/2012 | Webler et al. | 600/447 |
| 8,348,846 | B2 * | 1/2013 | Gunther et al. | 600/437 |
| 8,442,618 | B2 * | 5/2013 | Strommer et al. | 600/424 |
| 8,622,915 | B2 * | 1/2014 | Dala-Krishna | 600/466 |

(Continued)

*Primary Examiner* — Sanjay Cattungal

(57) ABSTRACT

Different intracardiac echocardiography volumes are stitched together. Different volumes of a patient are scanned with ICE. To stitch the volumes together, creating a larger volume, the volumes are spatially aligned. The alignment is based on feature, surface, or both feature and surface matching of the ICE volumes with a preoperative model of the same patient. The matching with the model indicates a relative position of the ICE volumes with each other. Using machine-trained classifiers may speed performance, allowing for real-time assembling of a volume from ICE data as the catheter is moved within the patient.

20 Claims, 3 Drawing Sheets

(56) References Cited

U.S. PATENT DOCUMENTS

| | | |
|---|---|---|
| 2004/0153128 A1* | 8/2004 | Suresh et al. .................. 607/14 |
| 2007/0014452 A1* | 1/2007 | Suresh et al. ................. 382/128 |
| 2007/0083111 A1* | 4/2007 | Hossack et al. ............... 600/437 |
| 2007/0156047 A1* | 7/2007 | Nagler et al. ................. 600/436 |
| 2008/0140180 A1* | 6/2008 | Dolan et al. ................. 623/1.13 |
| 2008/0146941 A1* | 6/2008 | Dala-Krishna ............... 600/466 |
| 2008/0177279 A1* | 7/2008 | Sumanaweera et al. ...... 606/130 |
| 2009/0005679 A1* | 1/2009 | Dala-Krishna ............... 600/437 |
| 2012/0113108 A1* | 5/2012 | Dala-Krishna ............... 345/419 |
| 2012/0165664 A1* | 6/2012 | Hill et al. ...................... 600/437 |
| 2012/0165672 A1* | 6/2012 | Hill et al. ...................... 600/443 |
| 2013/0064438 A1* | 3/2013 | Taylor et al. .................. 382/130 |
| 2013/0090554 A1* | 4/2013 | Zvuloni et al. ................ 600/424 |
| 2013/0138404 A1* | 5/2013 | Carbonera et al. ................ 703/2 |
| 2013/0173222 A1* | 7/2013 | Voth .................................. 703/1 |
| 2013/0173230 A1* | 7/2013 | Carbonera et al. ................ 703/2 |
| 2013/0216025 A1* | 8/2013 | Chan et al. ...................... 378/63 |
| 2014/0152653 A1* | 6/2014 | Dala-Krishna ............... 345/419 |

* cited by examiner

MODEL-BASED POSITIONING FOR INTRACARDIAC ECHOCARDIOGRAPHY VOLUME STITCHING

RELATED APPLICATIONS

The present patent document claims the benefit of the filing dates under 35 U.S.C. §119(e) of Provisional U.S. Patent Application Ser. No. 61/507,703, filed Jul. 14, 2011, which is hereby incorporated by reference.

BACKGROUND

The present embodiments relate to intracardiac echocardiography (ICE).

Percutaneous cardiac interventions are becoming more prevalent compared to "open" heart procedures. Percutaneous interventions may result in shorter patient recovery time and are considered a faster and less risky procedure. No anesthesia may be required.

During percutaneous cardiac interventions, clinicians may rely on one or more image acquisition techniques to guide the operation. ICE is one such technique. For example, the AccuNav ultrasound imaging catheter from Siemens Medical Solutions, USA, is used for ICE. This ultrasound catheter, with the small diameter size and long length, is able to be positioned in nearly every position in the heart chambers and record three or four-dimensional scans. The dynamic resolution is usually decent, but the spatial angle of the field of view may be small compared to the desired range. An experienced sonographer may recognize the important anatomical structures, guide the catheter inside the heart, and operate the device during the intervention. A wider field of view may make recognition of structures, guidance, and operation easier.

BRIEF SUMMARY

By way of introduction, the preferred embodiments described below include methods, computer readable media and systems for stitching intracardiac echocardiography volumes. Different volumes of a patient are scanned with ICE. To stitch the volumes together, creating a larger volume, the volumes are spatially aligned. The alignment is based on feature, surface, or both feature and surface matching of the ICE volumes with a preoperative model of the same patient. The matching with the model indicates a relative position of the ICE volumes with each other. Using machine-trained classifiers may speed performance, allowing for real-time assembling of a volume from ICE data as the catheter is moved within the patient.

In a first aspect, a method is provided for stitching intracardiac echocardiography volumes. First and second different cardiac volumes are scanned with ultrasound from a catheter within a patient. A model of at least a part of the cardiac system is acquired. The model is from preoperative data representing the part of the cardiac system. The first and second cardiac volumes are aligned with the model. Ultrasound data of the first and second cardiac volumes is combined into a third volume based on the aligning. An image of the part of the cardiac system is generated from the combined ultrasound data of the third volume.

In a second aspect, a non-transitory computer readable storage medium has stored therein data representing instructions executable by a programmed processor for stitching intracardiac echocardiography volumes. The storage medium include instructions for registering intracardiac echocardiography data from different scans with a physiological model, the model and the intracardiac echocardiography data being derived from a same patient, the different scans having an unknown relationship between coordinate systems, and generating a volume with a common coordinate system from the different scans as a function of the registering.

In a third aspect, a system is provided for stitching intracardiac echocardiography volumes. An ultrasound scanner is configured to scan with a catheter in a patient a plurality of volumes of the patient. The ultrasound scanner generates sets of ultrasound data representing the volumes. The volumes are for different regions of the patient. A processor is configured to generate a model of part of the patient from preoperative data scanned from the patient, to spatially register the sets of ultrasound data with the model, and to fuse the sets of ultrasound data as spatially registered.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Model-based fusion is performed for interoperative intracardiac echocardiography (ICE). Model-based registration allows for the fusing of multiple ICE volumetric data sets during cardiac interventions. Physiological models of the cardiac apparatus are extracted from one or more imaging modalities (e.g. computed tomography (CT), echo transesophageal (TEE), and/or magnetic resonance imaging (MRI)). This preoperative model derived specifically for the patient assists the data fusion process. The integration of the model and the ICE volume registration allows both estimation of a patient specific model with high accuracy and increased field of view for ICE.

In the inter-operative setting, the ICE images, which are acquired during the interventional procedure, are registered into a joint coordinate system with the pre-operative physiological model. Inaccuracies associated with using ICE intensities to register the volume may be avoided. Since the model is derived from preoperative data other than ICE for the specific patient, a physiological model accurately depicting the patient may assist in guidance and registration of ICE.

Figure 1:
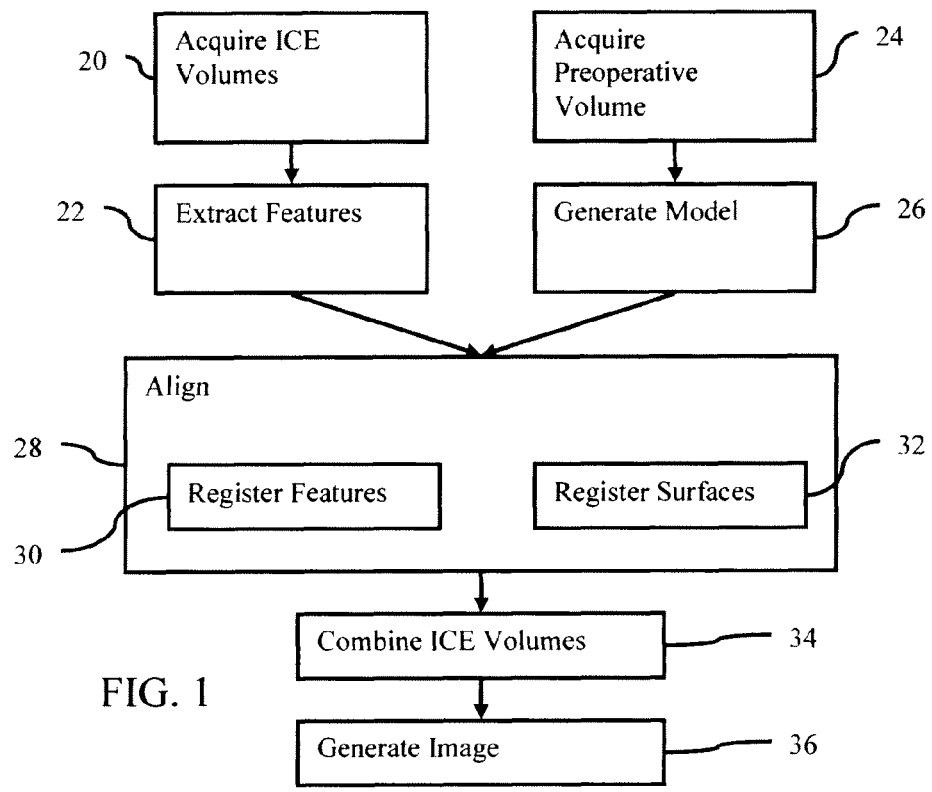
FIG. 1 is a flow chart diagram of one embodiment of a method for stitching intracardiac echocardiography volumes.

FIG. 1 shows a method for stitching intracardiac echocardiography volumes. The method is implemented by a medical diagnostic imaging system, a review station, a workstation, a computer, a PACS station, a server, combinations thereof, or other device for image processing medical diagnostic data. For example, the system or computer readable media shown in FIG. 4 implements the method, but other systems may be used.

The method is implemented in the order shown or a different order. For example, acts 20 and 22 are performed after acts 24 and 26, but simultaneous, interleaved or opposite order may be used. Additional, different, or fewer acts may be performed. For example, only one or both of acts 30 and 32 are performed. As another example, act 36 is not performed. In yet another example, act 24 and/or act 26 are not performed, but instead a previously created model for the patient is loaded from memory or received in a data transfer.

The acts are performed in real-time, such as during an intracardiac echocardiography procedure. The model may be created during or before the procedure. For example, the modeling is performed during an appointment or off-line in a review period prior to the intervention. The acquisition of ICE volumes in act 20, feature extraction of act 22, alignment of act 28, combination of act 34 and imaging of act 36 are performed during the procedure. Performing during the procedure allows the clinician to benefit from current wider angle views from within the heart. In other embodiments, the acts are performed after the procedure, such as performing as part of a review. In yet another embodiment, the generation of the model is performed as part of a joint solution with registration. The ICE volumes may contribute to the creation of the model while the model contributes to the alignment of the ICE volumes.

The acts may be performed automatically by a processor. The user causes the patient to be scanned or obtains scan data for the patient from a previous scan. The user may control the position of the catheter for acquiring the ICE volumes in act 20. The user may activate the process. Once activated, the ICE volumes are acquired in act 20, aligned in act 28, and combined in act 34. User input of locations of the anatomy or alignment in any of the scan data may be avoided. Some user input may be provided, such as for changing modeling parameter values, correcting detected locations, and/or to confirm accuracy.

A preoperative volume is acquired in act 24. The volume is a frame or set of data representing part or all of the heart. The data may represent other portions of the cardiac system, such as a valve, vessel, artery, and/or heart chamber. The data may alternatively or additionally represent all or parts of other organs, bone, or structure in the patient.

The data represents locations distributed in three dimensions. Multiple sets of data may be acquired over time, providing preoperative data representing four dimensions (e.g., three spatial and one temporal). The sets of 3D data in a 4D data set may be time stamped and/or associated with specific phases of a physiological cycle, such as the heart cycle. Where a 4D data set is acquired, the preoperative data is dynamic.

The preoperative data is acquired by scanning the patient prior to a procedure. For example, the patient is scanned in one room to acquire the preoperative data, and then the catheter is inserted in another room or the same room for the intervention procedure. The preoperative data may be acquired the same day or different day than the occurrence of the procedure.

The preoperative data is acquired using one or more modes of imaging. For example, transesophageal ultrasound data, magnetic resonance data, computed tomography data, or combinations thereof are acquired. Any scanning sequence or approach may be used, such as angiography modes or DynaCT. Since the preoperative data is acquired from the patient, the extracted model is a physiological model of the patient.

In an alternative embodiment, the preoperative volume is acquired by loading from memory. Data from a previously performed scan of the patient is stored in a memory, such as a picture archiving and communications system (PACS) database. The preoperative data is selected from the database. The preoperative volume may be acquired by transfer, such as over a network or on a portable memory device.

Figure 2:
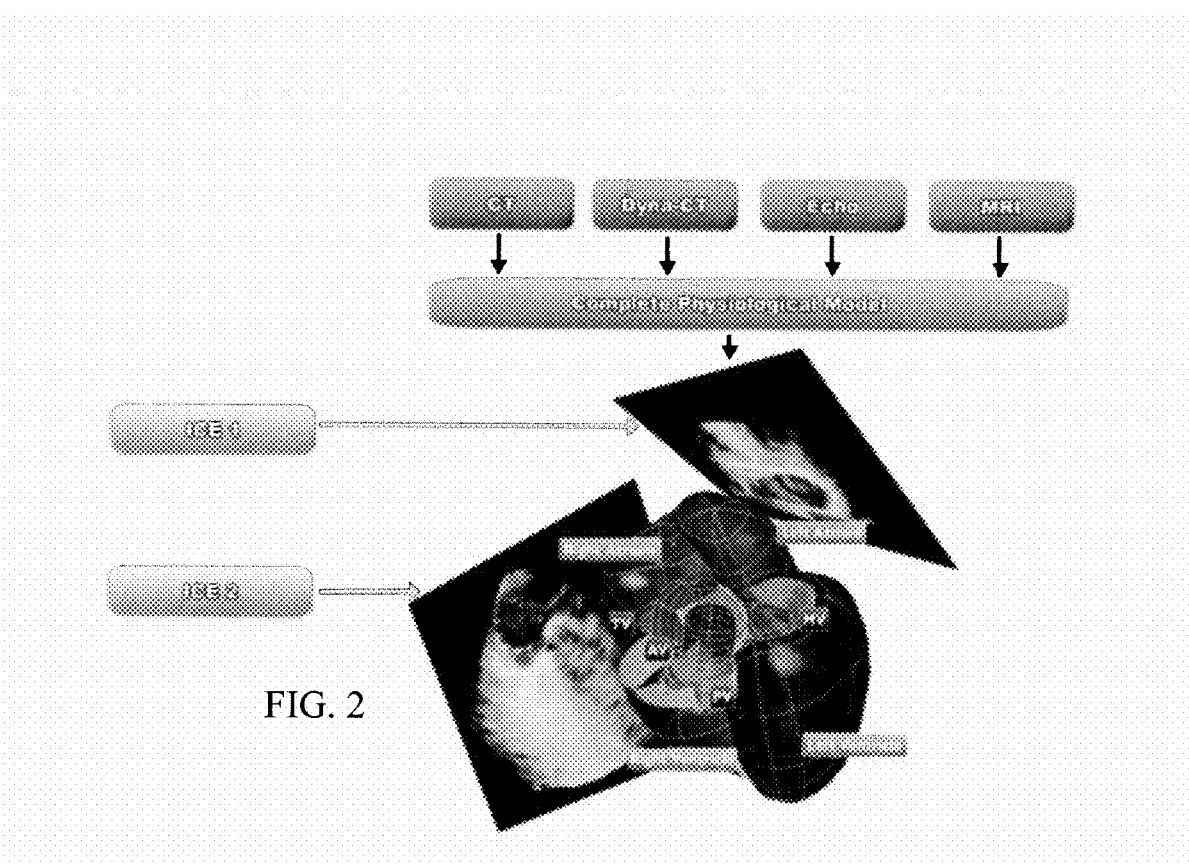
FIG. 2 is an illustration of another embodiment of the method for stitching intracardiac echocardiography volumes.

Referring to FIG. 2, a general example of the method for stitching is shown. Preoperative data, such as CT, DynaCT, TEE, and/or MRI are acquired. The preoperative data represents a larger region of the patient than a single ICE volume. For example, the preoperative data represents an entire heart and surrounding structure (e.g., tissue, such as the lungs, and bone, such as the sternum and ribs). The preoperative data may represent less than all of the heart.

In act 26 of FIG. 1, the model is generated from the preoperative data. The model is defined by one or more parameters. The parameters are characteristics of the model, such as spatial locations for points, lines, surfaces, landmarks, or other components of the model. The parameters are determined from the preoperative data.

Any modeling may be used. For example, a template is warped or transformed to fit the preoperative data. As another example, features and/or surfaces are detected from the preoperative data with one or more image processing approaches, such as segmentation, filtering, edge detection, pattern matching, or combinations thereof.

In one embodiment, the model is estimated using a machine-learnt detector or classifier. The machine-learnt classifier is trained before estimation of the model for a given patient, such as days, weeks, months, or years before.

A set of training data from different patients is acquired. The training data is the same type and for the same or similar region as the preoperative data. The training data is filtered or processed to obtain input features for the training or the training data itself is used as the input feature. Example input features for training include Haar and/or steerable features. A large pool of features may be extracted. The large pool is determined by a programmer or may include features systematically determined. The training determines the most determinative features for a given classification and discards lesser or non-determinative features.

To prepare the set of training samples, actual landmarks and/or surfaces in a number of images are manually annotated or indicated for use as a ground truth. Any number of expert annotated frames of data is used.

The detector is trained from the training data set using a computer. A data-driven, learning-based algorithm is applied to the training data. Using machine learning, the classifier is trained. The machine-trained classifier is any one or more classifiers. The classifier may be a model or detector using imaging processing, filtering, or other techniques. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

Only one classifier is applied to determine landmarks and/or surfaces. Alternatively, a series of classifiers are applied. A hierarchal or cascaded approach may be used, such as learning to detect landmarks and/or surfaces individually. The detector may be trained to detect groups or joint model parameters from the detected individual possibilities. The joint context associated with possible groups of landmarks, surface, nodes, meshes or other parameters may be used. The individual classifier, joint classifier, or both classifiers use a machine-learnt model or models.

In one embodiment, the machine-trained classifier is a probabilistic boosting tree classifier. The detector is a tree-based structure with which the posterior probabilities of the presence of the landmark and/or surface (e.g., nodes of a mesh) are calculated from given data. Each detector not only provides a binary decision for a given sample, but also a confidence value (e.g., score) associated with the decision. The nodes in the tree are constructed by a nonlinear combination of simple classifiers using boosting techniques. For example, the classifier has three levels with 40 weak classifiers at each node. The probabilistic boosting tree (PBT) unifies classification, recognition, and clustering into one treatment. Alternatively, a programmed, knowledge based, or other classifier without machine learning is used.

In one embodiment, a hierarchical approach is used. One or more bounding boxes are found to isolate the region and corresponding data of interest. A further detector is trained to detect specific landmarks within the bounding box or boxes from the data. Yet another detector is trained to locate surfaces based on the landmarks and the data.

Marginal space learning (MSL) or trajectory spectrum learning is used in one embodiment. For a static volume, MSL is applied. For 4D data, trajectory spectrum learning may train the detector to detect based on data from different times. The detectors are successively trained using the probabilistic boosting tree with Haar and steerable features.

Once trained, a matrix is output. The matrix represents the learnt algorithm for detection from preoperative data or features derived from the preoperative data. For application, the preoperative data or derived features from a specific patient are input to the matrix. As an output, the matrix indicates the location of one or more landmarks and/or surfaces. The output may also include probabilistic information, such as associated with alternative candidates for the location. The machine-learnt detector estimates the parameters of the model from the preoperative data.

The model includes landmarks and/or surfaces. The landmarks and/or surfaces are for the organ or part of the organ of interest. By applying the machine-learnt detector, the landmarks and surfaces of interest are located. The surfaces may be represented by a mesh, such as a collection of nodes and edges interconnecting the nodes. A rectangular mesh is used. Other meshes may be used, such as tetrahedral mesh.

In the example of FIG. 2, a physiological model is generated from the preoperative data. Using machine-learnt detection, landmarks and/or surfaces of the heart are found in the preoperative data. The model is based on scan data from a patient. This patient-specific modeling may result in the anatomy locations being different for different patients. For one patient, the relative locations of valve anatomy for a given time and/or the change in position over time may be different than for another patient. Patient-specific data is used to create the model. The model is represented in FIG. 2 as meshes for different parts of the heart as well as landmarks (e.g., mitral valve (MV), and left ventricle (LV)).

In act 20, different cardiac volumes are scanned with ultrasound. An ultrasound imaging catheter, such as the AccuNav catheter from Siemens Medical Solutions, USA, is inserted into the cardiac system. The catheter is guided to the region of interest. Using steering wires and/or a previously positioned guide, the transducer or transducer array in the catheter is positioned to scan a volume.

For scanning, electrical signals are transformed into acoustic signals. A beamformer generates the electrical signals. Using delays and/or apodization, a transmit beam of acoustic energy is generated. Acoustic echoes are received by the transducer or transducer array. Using electrical and/or mechanical steering, a volume of the patient is scanned. A receive beamformer samples the electrical signals generated by the transducer elements in response to the echoes. Using steering, the samples represent different locations in a polar coordinate format. The locations are distributed over three spatial dimensions.

Any field of view may be provided. For example, samples along a plurality of planes are generated. Within each plane, a 45-90 degree field of view may be provided. Across planes, the field of view is the same or different, such as being over 10-35 degrees. Any depth may be provided, depending on the frequency of the generated electrical signals. For example, a 5-10 cm depth is provided.

Any scan format may be used. For example, sector, Vector®, or linear planar or three-dimensional formats are used. The volume may be scanned by separately scanning different planes. The volume may be scanned with a three-dimensional scan pattern.

The receive beamformed samples are processed. The samples are detected. Any mode of detection may be provided, such as B-mode or flow mode (e.g., velocity, variance, or energy). Alternatively, the beamformed samples are used without detection. Filtering and scan conversion may be provided.

After acquiring the ultrasound data for a volume, the catheter and/or transducer are repositioned. The change in position may be by translating the transducer in any direction. Alternatively or additionally, the transducer is rotated. Due to the change in position, a different volume may be scanned.

In another embodiment, the change in position is ongoing as the catheter is navigated within the patient. The scanning continues, providing separate volumes that may or may not overlap. The volumes may have the same or different sizes. For example, an initial volume is of the entire field of view possible by the transducer. Subsequent volumes are for less field of view, such as acquiring data associated with parts of the patient not previously scanned. The subsequent volumes may or may not overlap with previous volumes. Different cardiac volumes are scanned with the intracardiac echocardiography catheter.

In the example of FIG. 2, two ICE volumes (ICE 1 and ICE 2) are acquired from different positions relative to a heart. The ICE volumes are shown as planes for simplicity, but are volumes. Ultrasound data representing a plurality of locations distributed in three-dimensions (e.g. x, y, and z, where x, y, and z are integers greater than 1) is provided for each ICE volume. Since the ICE volumes are from different perspectives, the coordinate systems may not align. Different coordinate systems result from the repositioning of the catheter for scanning the different ICE volumes.

In act 22, features represented by the ultrasound data of the cardiac volumes are detected. Any features may be detected, such as valves, ventricles, leaflets, flow regions, vessels, an apex of a chamber, an axis of a chamber, a heart wall, parts of heart structure, or collections of parts (e.g., joint feature detection). The detected features are landmarks for the portion of the body, such as for the heart. The landmarks are represented by the intracardiac echocardiography data, so may be extracted from the data. Since the data represents different locations relative to the transducer at a given position, the location of the landmarks is determined. Any number of features may be detected, such as eight features.

Figure 3:
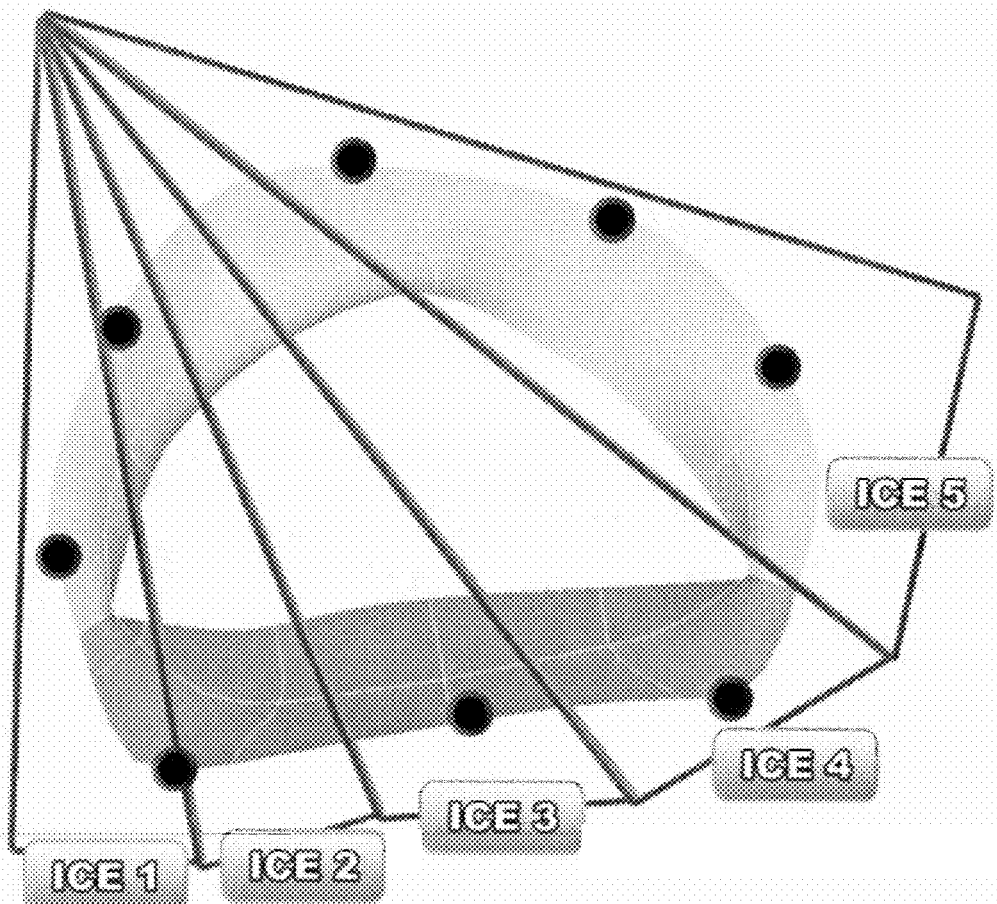
FIG. 3 is an illustration of example ICE volumes relative to a model.

Different volumes represent different features. The same feature may be detected in multiple volumes, such as where the volumes overlap. One or more, such as all, features in one volume may be represented in other volumes. FIG. 3 shows five ICE volumes associated with a mitral valve. The volumes are acquired by rotation of the transducer. The volumes are represented as planes due to the two-dimensional nature of the image sheet. In the example of FIG. 3, the volumes do not overlap. Different features or portions of features, shown as dots, are in different volumes. Two features are partly in two different volumes, ICE 1 and ICE 2. In other embodiments, none of the same features are in multiple ICE volumes.

The features are detected using a machine-learnt matrix. The same or different types of learning used for the model from the preoperative data may be used. The training data is ultrasound data from ICE volumes rather than the preoperative data. Since the features are extracted without determining surfaces, the hierarchal approach, if used, locates a bounding box and finds the feature or features within the bounding box. In one embodiment, a cascade of machine-trained classifiers is used. Input features for each classifier are calculated for each of the volumes. Each volume is tested for each of the features. The locations and/or volumes associated with the highest probability are used. Joint classification may be used to determine the arrangement or collection of features with relative positions most likely to occur.

The extraction of the features is performed to prepare for the alignment. Alternatively, the extraction is considered part of the alignment. Similarly, the generation of the model in act 26 may be considered part of the alignment.

In act 28, the different cardiac volumes acquired in act 20 are aligned. The relative spatial position is determined. With two ICE volumes, the difference in translation, rotation, and/or scale between the volumes is determined. Since the same transducer in a same imaging session may acquire the different volumes, the scale may be the same. Due to rotation, the coordinate systems of the different volumes may have an unknown relationship with each other. The rotation and/or translation between the volumes are determined in one embodiment.

The alignment includes interpolation to a common coordinate system. Due to the difference in rotation, the same sampling format may result in different coordinate systems for the different volumes. The various values for one volume do not represent locations on a regularly spaced three-dimensional grid with the other volume. Based on the alignment, the values for different locations are interpolated to a common three-dimensional grid. The common grid may be from one of the volumes, may be from the preoperative volume, or may be different than any of the volumes. The sampling density, type of spacing (e.g., rectangular or hexagonal), or grid variance (e.g., regular or variable) may be the same or different for the common grid and/or the different volumes. Any type of interpolation may be used, such as bilinear or trilinear. A nearest neighbor selection may be used instead. In other embodiments, the volumes are aligned without change in coordinate systems. Interpolation of the data representing the sample locations of the volumes is not performed.

The alignment uses the physiological model. Rather than use registration of the different ICE volumes with each other using intensities or rather than using self registration alone, the ICE volumes acquired in act 20 are aligned with the model generated in act 26. By aligning to a common reference (i.e., the model), the alignment of the ICE volumes with each other is determined.

The model from a same patient is used. Using scans of the same patient for both generating the model and the ICE scanning, patient specific differences may be captured and used for alignment, quantification, and/or visualization.

Referring to FIG. 2, the model is used to determine the spatial alignment of the ICE volumes. For example, the ICE volumes are shown as having specific positions relative to the model. This spatial registration is based on matching the ICE volumes to the model rather than each other. Registration based on correlation of ICE data may additionally be provided. Once registered, the ICE volumes may be fused or combined onto a common coordinate system for imaging and/or quantification.

The modeling and registration may be performed for any valve, the heart, a part of the heart, or other organ. In one embodiment, a single heart valve is identified and parameterized (see FIG. 3). In other embodiments, more than one heart valve or multiple parts of the heart are identified and parameterized at a same time or during a same imaging session. For example, the mitral valve and the aortic valve are physiologically modeled. The whole heart, half the heart, or other sub-portion of the heart may be scanned and modeled.

FIG. 3 shows an example alignment of the ICE volumes with the model. In the example of FIG. 3, the model is a mesh of nodes and interconnections representing a mitral valve. The mesh is shown as a grayed area with regularly spaced lines. The model also includes a plurality of landmarks or features of the mitral valve, represented as gray dots. Five ICE volumes (ICE1-5) are shown. The volumes are spaced adjacent to each other, such as associated with rotation of the transducer while being otherwise held in position.

The ultrasound data of the different ICE volumes also represents the landmarks. For the ICE volumes, the landmarks are represented as black dots overlaid on or aligned with the gray dots of the same landmarks from the model. The ultrasound data also represents the surface of the mitral valve, like the mesh but with intensity values from the scan. FIG. 3 represents the results of alignment with the patient-specific model.

Registration of the ICE volumes with the model is used to align. Any registration may be used. In one embodiment represented by act 30 of FIG. 1, features are used to register. The same landmarks are located in one or more of the ICE volumes and the model. Any landmarks may be used, such as anatomical landmarks. Other features may be used, such as locations at a particular spacing (e.g., nodes of a mesh).

To register an ICE volume with the model, the features represented by the ICE volume are used. The features determined in act 22 are registered with features generated as part of the model in act 26. The features of a given ICE volume are determined, such as by searching through a list of possible features. A cascaded classifier may be used to search for different features in any ICE volume.

The features of the ICE volume are translated, rotated, and/or scaled to best match the same features in the model. Rigid or non-rigid transformation may be used. Any correlation may be used. For example, different rotations, translations, and/or scales are tested and a measure of similarity quantified for each. The rotation, translation, and/or scale with the greatest similarity provide the relative difference or registration. In other embodiments, a probabilistic or machine-learnt approach is used. Based on training data and machine training, the features and locations from both the ICE volume and the model are input, and one or more alignments are output.

The registration aligns the features, such as anatomical landmarks, of the ICE volume with the model. The alignment is performed for each of the ICE volumes.

In another embodiment represented by act 32, surfaces are used for registering. The mesh or other representation of surface in the model is aligned with the ultrasound data of the ICE volume. The ultrasound data of the ICE volume represents any structure, including surfaces. Using correlation measures with translation, rotation, and/or scale searching or using machine-trained detection, the difference in position, rotation, and/or scale of the modeled surface with the ultrasound data of the ICE volume is calculated.

Each ICE volume may include, not include, or include only part of a given surface of the model. The search for each surface may be performed for all of the ICE volumes or all until found or all have been searched. The ICE volume or volumes with the highest correlation or greatest probability of match are selected as representing the surface.

The registration aligns the surfaces, such as anatomical surfaces, of the ICE volume with the model. The alignment is performed for each of the ICE volumes.

Other alignment approaches may be used. In one embodiment, a combination of different approaches is used. Both image intensities and preoperative dynamic physiological features guide the registration process. For example, feature-based and surface-based alignments are performed. To use multiple alignments, the alignments are performed sequentially, such as using feature-based alignment to coarsely align and then using surface-based alignment to refine. The coarse alignment is used to limit the search region of the surface-based alignment. The opposite order may be used, such as aligning first using surfaces and then using features.

In another embodiment, an iterative approach is used. The alignments are repeated sequentially until convergence. Each previous alignment is used to limit the search space of the next alignment.

In yet another embodiment, an iterative solution is based on a probabilistic formulation where both feature extraction for the ICE volume and/or the model is performed with the alignment. The registration uses the features and surfaces in an estimation maximization (EM) framework.

To jointly extract features and determine alignment, an initial mean model is estimated from features extracted from the ICE volumes. The mean model is an affine or other transformation of the model generated in act 26 to the ICE volumes. The model is deformed or warped to account for differences in the patient over time (i.e., between acquiring the preoperative data and the ICE volumes).

After initial deformation, joint segmentation and registration is applied to refine the initial model and register the images into a common coordinate system. In the joint segmentation and registration, a probabilistic formulation is used to describe the registration problem. The estimation maximization framework is applied to estimate the final registration and model parameters. The model is both registered with the ICE volume and deformed in an iterative approach. The deformation alters the model for a next iteration of the registration. Once convergence is reached, both the model and the registration are complete. In the example of FIG. 3, the result is an accurate patient-specific model of the mitral valve and five registered ICE volumes of the mitral valve.

In act 34, the ultrasound data from the different ICE volumes is combined or fused. The alignment indicates the relative spatial position. The combination uses the relative spatial position to combine the ICE volumes into a larger volume. In the example of FIG. 3, the relative position of the five ICE volumes is shown. As shown, these positioned ICE volumes form a combined volume.

The combined volume has a common coordinate system or is a combination of the volumes without interpolation to a common coordinate system. For a common coordinate system, the ultrasound data of the ICE volumes is interpolated to the common coordinate system. A volume is generated with ultrasound data from different ICE volumes interpolated to a single volume with a same coordinate system. The alignment is used to determine which of the ultrasound data to interpolate to any given point.

Where the volumes do not overlap, the combination is performed without summing, multiplying or otherwise mathematically combining the ultrasound data from different ICE volumes. Where the ICE volumes overlap, the ultrasound data may be mathematically combined. Data from different volumes representing a same location are averaged. Selection of one value from among several volumes may be used. Other mathematical combination than averaging may be used. The mathematical combination may occur as part of interpolation, prior to interpolation, or after interpolation to a common grid.

In a real-time embodiment, an initial pair of ICE volumes is combined based on registration with a preoperative model. Subsequently acquired ICE volumes are registered with the preoperative model and combined with the existing combined ICE volume (already combined volume).

When combining ICE volumes of structure subjected to cyclic motion, such as the heart, gating or triggering may be used. Gating selects ultrasound data from a sequence for combination. Triggering causes acquisition of volumes for the desired phase. The combination is performed for ICE volumes representing a same phase of the cycle. Other combined volumes may be formed for other phases. In alternative embodiments, the fusion accounts for motion by motion correction between ICE volumes for different phases. Ultrasound data from different phases may be combined.

In act 36, an image is generated. The image is generated from the combined ultrasound data. The image represents parts of the patient from different ICE volumes. At least one location represented by the image is from ultrasound data of one ICE volume and not another. Another location represented in the image is from ultrasound data for the other ICE volume and not the one ICE volume. One or more locations may be represented by both ICE volumes. The image represents an extended field of view not available with a single ICE volume. The image is formed from the combined ultrasound data of the combined ICE volumes.

The image is formed from the ultrasound data interpolated to the same coordinate system. In one embodiment, the coordinate system of the physiological model is used for the common coordinate system. The ultrasound data from the ICE volumes may be transformed to a common coordinate system with the preoperative data. In other embodiments, the image is generated by selection or combination of values from the ultrasound data in different coordinate systems. The formation of the image regularizes the spatial distribution. Alternatively, scan conversion after formation of the image regularizes the spatial distribution. The image is generated in a format for the display device.

Any type of image may be generated. For example, the image is three-dimensionally rendered from the combined volume. Using a user or processor selected point of view with or without a lighting model, the ultrasound data representing the combined volume is rendered to a two-dimensional display. Any volume rendering may be used, such as projection or surface rendering. In another example, a planar reconstruction is generated from the ultrasound data. A user or processor placed slice plane or image plane is positioned relative to the volume. The ultrasound data representing or interpolated to represent the plane is used to generate the two-dimensional image. For multi-planar reconstruction, multiple planes are defined through the volume. An image is generated for each plane. In the heart example, the multiple planes may correspond to standard heart views that are generally orthogonal to each other.

The image from the ICE volumes is shown alone. A sequence of such images may be shown, such as rendering from a sequence of combined volumes from different phases of a heart cycle. Alternatively, the image or images are shown with other information. The image may be separate but share the display screen with an image generated from the preoperative data and/or the model. The model may be overlaid on the image, such as rendering the model with a different color, brightness or other characteristic. The rendered model is added to the image for generating the overlay.

In alternative or additional embodiments, the combined volume is used for quantification. A volume, area, length, or other quantity is calculated from the ultrasound data of the combined volume. For example, a value representing operation or other characteristic of the valve is calculated from the surface at a given time or from surfaces from different phases.

Figure 4:
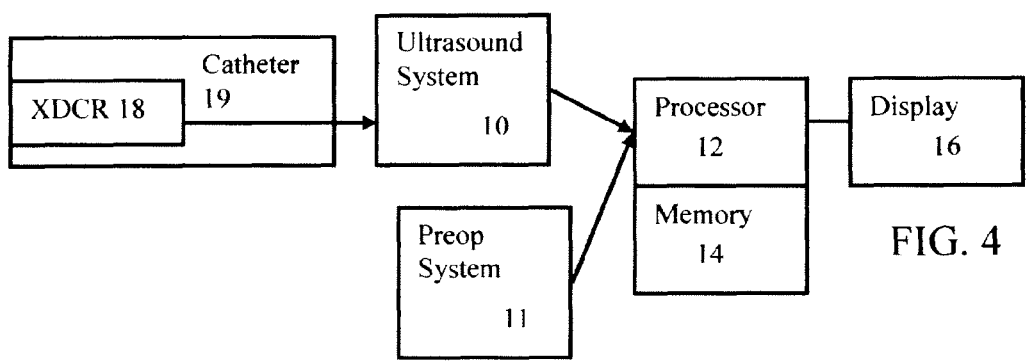
FIG. 4 is a block diagram of one embodiment of a system for stitching intracardiac echocardiography volumes.

FIG. 4 shows a system for stitching intracardiac echocardiography volumes. The system includes a catheter 19, a transducer 18, an ultrasound scanner 10, a preoperative system 11, a processor 12, a memory 14, and a display 16. The preoperative system 11 and the ultrasound scanner 10 are shown as separate systems, but may be the same system. For example, the ultrasound scanner 10 is used for a TEE scan to acquire preoperative data as well as for the ICE scans with the catheter 19. The processor 12 and the memory 14 are shown separate, such associated with being a computer or workstation apart from the ultrasound scanner 10 and the preoperative system 11. In other embodiments, the processor 12 and/or memory 14 are part of the ultrasound scanner 10 or the preoperative system 11. In alternative embodiments, the system is a workstation, computer, or server for stitching volumes using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for creating a model, detecting anatomy, and/or validating the model. Additional, different, or fewer components may be used.

The computing components of the system, such as the ultrasound scanner 10, the preoperative system 11, and/or the processor 12 are configured by hardware, software, and/or design to perform calculations or other acts. The computing components operate independently or in conjunction with each other to perform any given act. The act is performed by one of the computer components, another of the computing components, or a combination of the computing components. Other components, such as the transducer 18, may be used by the computing components to scan or perform other functions.

The ultrasound scanner 10 includes a transmit beamformer, receive beamformer, B-mode detector, Doppler detector, harmonic response detector, contrast agent detector, scan converter, filter, combinations thereof, or other now known or later developed medical diagnostic ultrasound system components. The ultrasound scanner 10 connects with or releasably connects with the transducer 18.

The transducer 18 is a piezoelectric or capacitive device operable to convert between acoustic and electrical energy. The transducer 18 is an array of elements, such as a multi-dimensional (e.g., two-dimensional) array. In one embodiment, the array of elements is a 1.5 or 1.75 D array for limited elevation scanning to scan multiple planes or a volume. In another embodiment, the array of elements is a one dimensional array with the elements twisted in a helical pattern so that different apertures spaced along the array scan in different planes, providing a volume scan. Alternatively, the transducer 18 is a wobbler or rotatable for mechanical scanning in one dimension and electrical scanning in another dimension to scan a volume. A plurality of one-dimensional arrays may be provided to scan the volume.

The transducer 18 is within or on the catheter 19. The catheter is a cardiac catheter, such as being 15 french or less in diameter and extending for a plurality of feet for insertion of the transducer 18 into the heart of the patient. Any ICE imaging catheter may be used.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rotating an array, moving a catheter array, or volume scanning with a volume scanning array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart, part of the heart, valve (e.g., mitral valve), or other location. The scan is of a volume. By rotating and/or translating the catheter 19, the transducer 18 scans a different volume. Volumes of at least some different anatomy are scanned at different times.

A single scan is provided for each volume. Alternatively, each volume is scanned multiple times as a sequence. The scan is repeated to provide data for the volume at different times.

A frame or set of ultrasound data representing a volume is provided in response to the scanning. Each frame represents the scan region at a given time or over a period. Different frames are provided for different volumes. Different frames are provided for repetition of the scans for a same volume.

The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., Doppler or color mode), contrast agent, harmonic, or other ultrasound modes of imaging.

The preoperative system 11 is a CT, MR, x-ray, angiography, fluoroscopy, PET, SPECT, or ultrasound system. The preoperative system 11 is configured to acquire the preoperative data for modeling. The data is acquired by scanning the patient and/or by receiving signals from the patient.

The memory 14 is a buffer, cache, RAM, removable media, hard drive, magnetic, optical, database, or other now known or later developed memory. The memory 14 is a single device or group of two or more devices. The memory 14 is within the system 10, the system 11, part of a computer with the processor 12, or is outside or remote from other components.

The memory 14 stores the ultrasound data, such as ICE volumes of ultrasound data representing a heart volume, valve volume, or other volume. The heart volume includes at least one valve, but other portions of the heart may be represented. The memory 14 stores preoperative data representing a volume. The preoperative data represents a larger volume or portion of the patient than any one ICE volume. The preoperative and ultrasound data form three-dimensional data sets, or a sequence of such sets. The data represents a three-dimensional region. Any format may be used, such as voxels interpolated to a three-dimensional grid or data representing parallel or non-parallel planes.

For real-time imaging, the ultrasound data bypasses the memory 14, is temporarily stored in the memory 14, or is loaded from the memory 14. Real-time imaging may allow delay of a fraction of a second, or even seconds, between acquisition of data and imaging with measurements. For example, real-time imaging is provided by generating the images substantially simultaneously with the acquisition of the data by scanning. While scanning to acquire a next or subsequent set of data, processing, combining, imaging, and/or measuring are preformed using a previous set or sets of data. The imaging occurs during the same imaging session or patient appointment used to acquire the data for real-time imaging. The amount of delay between acquisition and imaging for real-time operation may vary, such as a greater delay for initially generating the model with less delay for subsequent registration of ICE volumes with the model. In alternative embodiments, the ultrasound data is stored in the memory 14 from a previous imaging session and used without concurrent acquisition.

The memory 14 is additionally or alternatively a non-transitory computer readable storage medium with processing instructions. The memory 14 stores data representing instructions executable by the programmed processor 12 for stitching intracardiac echocardiography volumes. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 operates pursuant to stored instructions to perform various acts described herein.

The processor 12 is configured to generate a model of part of the patient from preoperative data scanned from the patient. The processor 12 controls the preoperative scanning or accesses data acquired from scanning using other control. For example, the processor 12 is part of the ultrasound scanner 10 and controls acquisition of TEE ultrasound data. As another example, the processor 12 accesses data from an archive or scanning system (e.g., preoperative system 11).

The processor 12 is configured to apply a machine trained detector to the preoperative data. The machine-trained detector outputs landmarks and/or surfaces. In one embodiment, the machine-trained detector jointly determines landmarks and/or surfaces with registration of the landmarks and/or surfaces with ICE ultrasound data.

The processor 12 is configured to spatially register the sets of ultrasound data with the model. The surfaces of the model are aligned with the ultrasound data, such as using measures of similarity. The landmarks of the model are aligned with landmarks extracted from the ultrasound data, such as aligning using measures of similarity. Both landmarks and surfaces may be used jointly for aligning. Using a machine-trained classifier, the alignment may be detected using probabilities based on input features (e.g., landmarks and Haar or steerable features for surface detection).

The processor 12 may perform machine learning and/or applies a machine-learnt algorithm. For example, the processor 12 applies a probabilistic model to detect anatomy, register, or both. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different anatomy or types of motion. The probabilistic models may be joint or dependent. The location of other anatomies is used to limit or define a search space for a current anatomy and/or as a feature input for classification of another anatomy.

The different classifiers for joint classification, marginal space classification, and/or multiple resolution classification are the same or different types of classifiers. The same or different types of classifiers may be used for the same type of classification, such as different types of classifiers being used for different marginal space classification (e.g., the classifier for finding a region is different than the classifier for landmark and/or surface location determination within the region).

In one embodiment, the probabilistic model is formed from a plurality of probabilistic boosting tree classifiers. Separate training and resulting machine-trained classifiers are provided for each type of landmark and/or surface of interest. For each of these separate classifiers, separate probabilistic boosting tree classifiers are provided for each of the marginal space types. For example, the classifiers follow the marginal space learning protocol.

For application, the processor 12 calculates features for classification. The same or different features are used for classification in each stage. The features are three-dimensional features. 3D data is used to calculate the features. A window function defining the data is a cube, but may have other volume shapes. The window is translated, rotated, and scaled as part of searching for an anatomy. The same or different sized windows are used for different anatomies.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. In one embodiment, the type of features used is gradient features. For example, the "steerable" features are used. Other types of features may alternatively or additionally be used.

The processor 12 is configured to fuse the sets of ultrasound data as spatially registered. The alignment of the sets of ultrasound data with the model provides a relative alignment for the sets of ultrasound data with each other. The relative alignment is used to fuse the sets into a volume extending over an expanded field of view. In one embodiment, the fusion interpolates the ultrasound data of the sets to a common coordinate system. The fusion may additionally or alternatively be used to filter or combine data representing the same or similar locations.

The processor 12 is configured to generate an image. The image is generated as a function of the fused sets of ultrasound data. Where the fusion is the relative alignment, this offset may be used to select data to be used for imaging. Where the fusion is a set of data on a common coordinate system, the fused set of data may be used to image. The image is a volume or three-dimensional rendering. Alternatively, the image is of an arbitrarily positioned plane or planes through the fused volume. The plane or planes may have any orientation, including orientations within the volume different than the scanning lines or planes.

The display 16 is a CRT, LCD, plasma, projector, printer, or other output device for showing an image. The display 16 displays an image of the fused volume. The image represents locations not available from a single ICE scan volume. A value of a measurement may be displayed. The value may be displayed in a chart, graph, and/or on an image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for stitching intracardiac echocardiography volumes, the method comprising:
scanning first and second different cardiac volumes with ultrasound from a catheter within a patient;
acquiring a model of at least a part of the cardiac system, the model being from preoperative data representing the part of the cardiac system;
aligning the first and second cardiac volumes with the model;
combining ultrasound data of the first and second cardiac volumes into a third volume based on the aligning; and
generating an image of the part of the cardiac system from the combined ultrasound data of the third volume.

2. The method of claim 1 wherein scanning comprises scanning with the catheter comprising an intracardiac echocardiography catheter.

3. The method of claim 1 wherein scanning comprises scanning the first cardiac volume, moving the catheter, and scanning the second cardiac volume, the first cardiac volume overlapping the second cardiac volume.

4. The method of claim 1 wherein acquiring the model comprises acquiring the model as a plurality of surfaces and landmarks.

5. The method of claim 1 wherein acquiring the model comprises acquiring from the preoperative data comprising transesophageal ultrasound data, magnetic resonance data, computed tomography data, or combinations thereof.

6. The method of claim 1 wherein acquiring the model comprises estimating parameters of the model from the preoperative data with a machine-learnt detector.

7. The method of claim 1 wherein aligning comprises:
detecting first and second features in the first and second cardiac volumes, respectively; and
registering the first and second features with third and fourth features of the model.

8. The method of claim 1 wherein aligning comprises:
registering first and second surfaces of the model with the ultrasound data of the first and second volumes.

9. The method of claim 8 wherein aligning also comprises:
detecting first and second features in the first and second cardiac volumes, respectively;
registering the first and second features with third and fourth features of the model; and
iteratively solving for an alignment using the registering of the first and second features and the first and second surfaces.

10. The method of claim 9 further comprising:
initializing the aligning by deforming the model to the first and second features.

11. The method of claim 1 wherein combining comprises interpolating to a same coordinate system.

12. The method of claim 1 wherein generating comprises three-dimensionally rendering the image or generating a multi-planar reconstruction from the combined ultrasound data of the third volume.

13. In a non-transitory computer readable storage medium having stored therein data representing instructions executable by a programmed processor for stitching intracardiac echocardiography volumes, the storage medium comprising instructions for:
registering intracardiac echocardiography data from different scans with a physiological model, the model and the intracardiac echocardiography data being derived from a same patient, the different scans having an unknown relationship between coordinate systems; and
generating a volume with a common coordinate system from the different scans as a function of the registering.

14. The non-transitory computer readable storage medium of claim 13 wherein registering comprises:
extracting landmarks represented by the intracardiac echocardiography data; and
aligning the landmarks with the model.

15. The non-transitory computer readable storage medium of claim 13 wherein registering comprises:
correlating surfaces of the model with the intracardiac echocardiography data;
aligning based on the correlating.

16. The non-transitory computer readable storage medium of claim 13 wherein generating comprises interpolating the intracardiac echocardiography data to the common coordinate system.

17. A system for stitching intracardiac echocardiography volumes, the system comprising:
an ultrasound scanner configured to scan with a catheter in a patient a plurality of volumes of the patient, the ultrasound scanner generating sets of ultrasound data representing the volumes, the volumes being for different regions of the patient; and
a processor configured to generate a model of part of the patient from preoperative data scanned from the patient, to spatially register the sets of ultrasound data with the model, and to fuse the sets of ultrasound data as spatially registered.

18. The system of claim 17 wherein the processor is configured to generate the model by acquiring the preoperative data as transesophageal ultrasound data, magnetic resonance data, computed tomography data or combinations thereof and applying a machine trained detector to the preoperative data, the machine trained detector outputting landmarks and surfaces; and
configured to spatially register by aligning the surfaces of the model with the ultrasound data, aligning the landmarks with landmarks extracted from the ultrasound data, and jointly solving from both alignments using probabilities.

19. The system of claim 17 wherein the processor is configured to fuse by interpolating the ultrasound data of the sets to a common coordinate system.

20. The system of claim 17 wherein the processor is configured to generate an image as a function of the fused sets of ultrasound data.

* * * * *